US00PP22202P2

(12) United States Plant Patent
van Kleinwee

(10) Patent No.: US PP22,202 P2
(45) Date of Patent: Oct. 18, 2011

(54) ***PETUNIA* PLANT NAMED 'PETREWIS'**

(50) Latin Name: *Petunia hybrida*
Varietal Denomination: Petrewis

(75) Inventor: Theodorus Cornelis Maria van Kleinwee, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/802,831

(22) Filed: Jun. 15, 2010

(51) Int. Cl.
*A01H 5/00* (2006.01)

(52) U.S. Cl. ..... Plt./356.23

(58) Field of Classification Search ..... Plt./356, Plt./356.23
See application file for complete search history.

*Primary Examiner* — Susan McCormick Ewoldt
(74) *Attorney, Agent, or Firm* — S. Matthew Edwards

(57) ABSTRACT

A new *Petunia* plant named 'Petrewis' particularly distinguished by the medium sized bold deep-red flowers, early flowering and good floriferousness, medium green foliage, excellent branching, and an outwardly spreading plant habit with exceptional cold tolerance.

1 Drawing Sheet

Latin name of the genus and species of the plant claimed: *Petunia hybrida.*

Varietal denomination: 'Petrewis'.

BACKGROUND OF THE NEW PLANT

The present invention comprises a new *Petunia,* botanically known as *Petunia hybrida,* and hereinafter referred to by the variety name 'Petrewis'.

'Petrewis' is a product of a planned breeding program. The new cultivar has medium sized bold deep-red flowers, early flowering and good floriferousness, medium green foliage, excellent branching, and an outwardly spreading plant habit with exceptional cold tolerance.

'Petrewis' originated from a hybridization made in August 2005 in a controlled breeding environment in Enkhuizen, Netherlands. The female parent was a bulk population of plants from a proprietary, unpatented population designated 'E5327', that had flowers ranging in color from red to dark salmon. The seed was harvested in bulk and sown in February 2006.

The male parent of 'Petrewis' was a proprietary, unpatented population designated as 'B1256-1', with burgundy flowers.

'Petrewis' was selected as one flowering plant within the progeny of the stated cross in May 2006, in a controlled environment in Enkhuizen, Netherlands.

The first act of asexual reproduction of 'Petrewis' was accomplished when vegetative cuttings were propagated from the initial selection in May 2006 in a controlled environment in Enkhuizen, Netherlands.

BRIEF SUMMARY OF INVENTION

Horticultural examination of plants grown from cuttings of the plant initiated in May 2006, and continuing thereafter, has demonstrated that the combination of characteristics as herein disclosed for 'Petrewis' are firmly fixed and are retained through successive generations of asexual reproduction.

'Petrewis' has not been observed under all possible environmental conditions. The phenotype may vary significantly with variations in environment such as temperature, light intensity and day length.

A Plant Breeder's Right for this cultivar was applied for in Canada on Feb. 9, 2010 (#10-6829). 'Petrewis' has not been made publicly available more than one year prior to the filing of this application.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawing shows typical flower and foliage characteristics of 'Petrewis' with colors being as true as possible with an illustration of this type. The photographic drawing shows a flowering potted plant of the new variety and a close-up of the flowers growing in a 4 inch pot.

DETAILED BOTANICAL DESCRIPTION

The plant descriptions, measurements and aforementioned photographs were taken in Gilroy, Calif. from plants growing in a greenhouse trial in April 2010. These plants were approximately 13-14 weeks of age.

Color references are made to The Royal Horticultural Society Colour Chart (R.H.S.) 2001.

TABLE 1

DIFFERENCES BETWEEN THE NEW VARIETY 'PETREWIS' AND A SIMILAR VARIETY

| | 'Petrewis' | 'Whip Reeda' (U.S Plant Pat. No. 16,610) |
|---|---|---|
| Foliage size: | Larger | Smaller |
| Petiole length: | Longer | Shorter |
| Petiole texture: | Glandular hairs | Glandular hairs and hirsute |
| Bud color: | RHS 183D | RHS 182B |

Plant:

*Form, growth and habit.*—Initially somewhat upright, then outwardly spreading plant habit, excellent branching, early flowering habit, exceptional cold tolerance.

*Plant height.*—About 10 cm.
*Plant height (inflorescence included).*—15-18 cm.
*Plant width.*—36-40 cm.
*Garden performance and tolerance to weather.*—Very good.
*Crop time to flowering.*—About 8-9 weeks.

Roots:
*Number of days to initiate roots and produce a rooted cutting.*—18-23 days at about 22 degrees C.
*Type.*—Fine, fibrous, free branching.
*Color.*—RHS N155B but whiter.

Foliage:
*Arrangement.*—Alternate, upper leaves sub-opposite.
*Immature, leaf color, upper surface.*—RHS 137A.
*Lower surface.*—Between RHS 146B and RHS 146C.
*Mature, leaf color, upper surface.*—RHS 137A.
*Lower surface.*—Between RHS 146B and RHS 146 C.
*Length.*—4.7-6.6 cm.
*Width.*—3.4-5.0 cm.
*Shape.*—Ovate.
*Base shape.*—Acuminate.
*Apex shape.*—Acute.
*Margin.*—Entire.
*Texture, upper surface.*—Glandular hairs.
*Lower surface.*—Glandular hairs.
*Color of veins, upper surface.*—Between RHS 144A and RHS 144B.
*Color of veins, lower surface.*—RHS 144A.
*Petiole color.*—Between RHS 144A and RHS 144B.
*Length.*—1.0-3.0 cm.
*Diameter.*—0.3-0.5 cm.
*Texture.*—Glandular hairs.

Stem:
*Color of stem.*—RHS 144A.
*Length of stem.*—15-20 cm.
*Diameter.*—0.5-0.6 cm.
*Length of internodes.*—2.0-3.5 cm.
*Texture.*—Glandular hairs.
*Color of peduncle.*—RHS 144A but a little lighter.
*Length of peduncle.*—2.0-2.5 cm.
*Peduncle diameter.*—0.20 cm.
*Texture.*—Glandular hairs.

Inflorescence:
*Type.*—Flowers appear solitary in upper leaf axis.
*Floret type.*—Funnel-shaped; 5 lobed petals; fused at the base; calyx, 5 deeply lobed sepals.
*Blooming habit.*—Continuous throughout the growing season. Good floriferousness.
*Quantity of inflorescences per plant.*—85 plus numerous buds.
*Lastingness of individual blooms on the plant.*—5-7 days.
*Fragrance.*—Slightly sweet.

Bud (just before opening/showing color):
*Color.*—RHS 183D with RHS 183C veins.
*Length.*—3.0-4.0 cm.
*Width.*—0.5-0.7 cm.
*Shape.*—Oblong.

Immature inflorescence:
*Diameter.*—4.5 cm.
*Color, upper surface.*—Closest to RHS 45B.
*Lower surface.*—Closest to RHS 185D.

Mature inflorescence:
*Floret horizontal diameter.*—5.3-5.5 cm.
*Vertical depth.*—4-4.5 cm.
*Petal color, upper surface.*—Closest to RHS 45B with RHS N77A mid veins and RHS 53A veins.
*Lower surface.*—Between RHS 185D and RHS 186D with RHS 166A mid veins and RHS 165A veins.
*Petal apex shape.*—Cuspidate.
*Petal base shape.*—Fused.
*Petal margin.*—Entire.
*Waviness of petals.*—Moderate.
*Petal lobation.*—Moderate.
*Petal texture, upper surface.*—Papillose.
*Under surface.*—Papillose.
*Corolla tube color inside.*—RHS 182D base color heavily overlaid with RHS 183C veining.
*Outside.*—Closest to RHS 183D but greyer.
*Corolla tube length.*—2.5 cm.
*Corolla texture, inside.*—Papillose.
*Outside.*—Glandular hairs; pilose.

Calyx:
*Quantity of sepals.*—5.
*Color, upper surface.*—RHS 138A but more green.
*Lower surface.*—RHS 138A but more green.
*Length.*—1.7-1.8 cm.
*Width.*—0.3-0.35 cm.
*Shape.*—Ligulate.
*Apex shape.*—Obtuse.
*Based.*—Fused.
*Margins.*—Entire.
*Texture, upper surface.*—Glandular hairs.
*Lower surface.*—Glandular hairs.

Reproductive organs:
*Pistil.*—1.
*Length.*—1.4 cm.
*Style color.*—RHS 139D but lighter.
*Style length.*—1.2 cm.
*Stigma color.*—RHS 139C.
*Stigma shape.*—Oval.
*Ovary color.*—RHS 143B.
*Stamens.*—5.
*Color of filaments.*—RHS 182D but lighter.
*Length of filaments.*—1.5 cm.
*Anther color.*—RHS 155A.
*Anther length.*—0.2 cm.
*Anther shape.*—Oval.
*Color of pollen.*—RHS 155C.
*Pollen amount.*—Good.
*Fertility/seed set.*—Has not been observed on this hybrid.

Disease/pest resistance: Disease/pest resistance has not been observed on this hybrid.

What is claimed is:

1. A new and distinct variety of *Petunia* plant named 'Petrewis' substantially as illustrated and described herein.

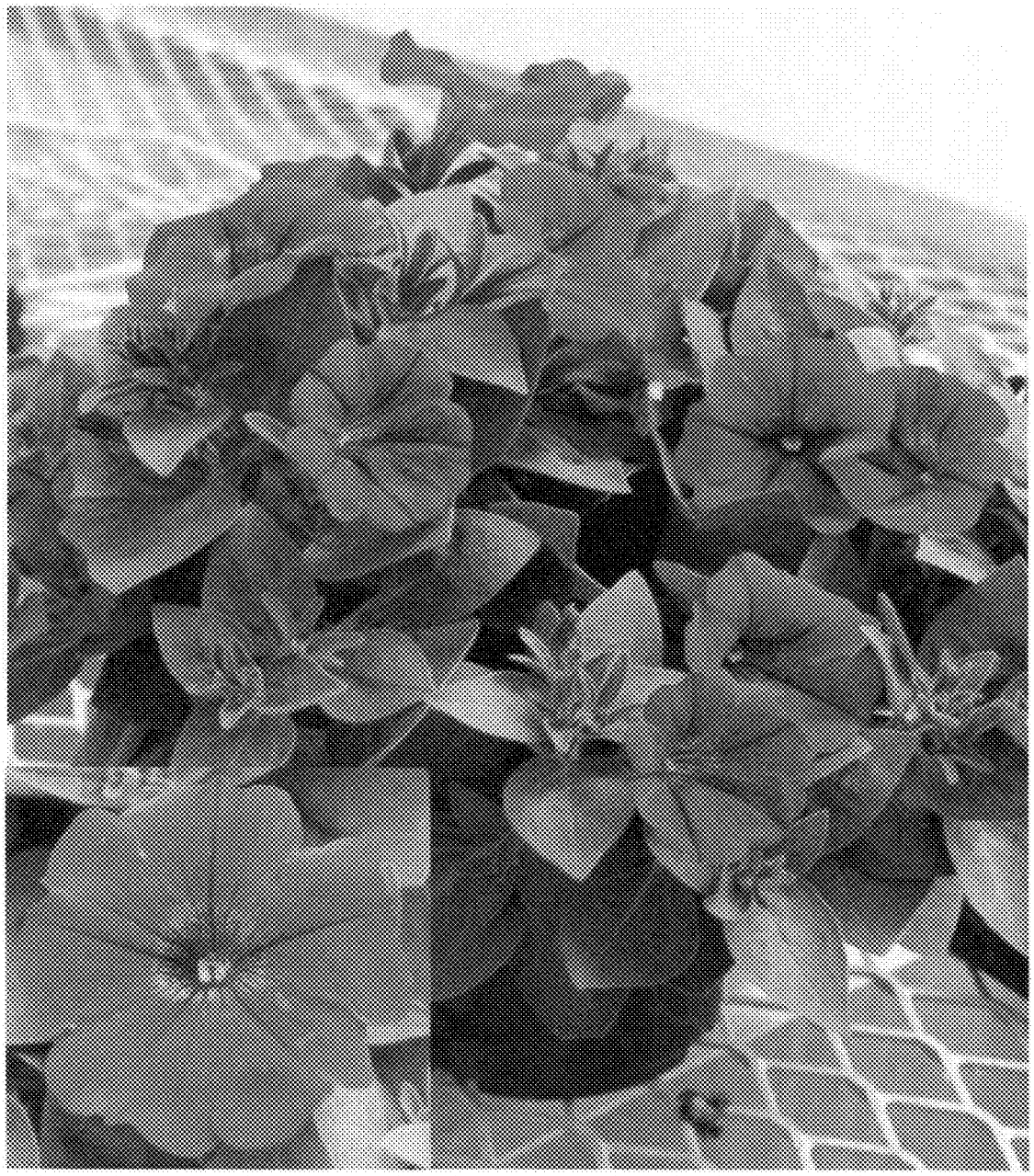

* * * * *